(12) United States Patent
Arnold et al.

(10) Patent No.: US 8,765,082 B2
(45) Date of Patent: Jul. 1, 2014

(54) COMBINED CARBON DIOXIDE AND OXYGEN PROCESS FOR ETHYLBENZENE DEHYDROGENATION TO STYRENE

(75) Inventors: Stephen C. Arnold, Mountain Lakes, NJ (US); Johannes Hendrik Koegler, Montclair, NJ (US); Anne Mae Gaffney, West Chester, PA (US); Chuen Yuan Yeh, Edison, NJ (US); Ruozhi Song, Wilmington (DE)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 13/567,207

(22) Filed: Aug. 6, 2012

(65) Prior Publication Data

US 2012/0294776 A1   Nov. 22, 2012

Related U.S. Application Data

(62) Division of application No. 12/142,738, filed on Jun. 19, 2008, now Pat. No. 8,237,000.

(51) Int. Cl.
*B01J 8/02* (2006.01)
*C07C 5/48* (2006.01)

(52) U.S. Cl.
USPC ........... 422/608; 422/617; 422/630; 422/211; 422/239; 585/443; 585/621; 585/633

(58) Field of Classification Search
None
See application file for complete search history.

(56) References Cited

U.S. PATENT DOCUMENTS

| | | | |
|---|---|---|---|
| 2,604,495 A | | 7/1952 | Erkko |
| 3,375,288 A | * | 3/1968 | De Rosset .................... 585/403 |
| 3,847,968 A | * | 11/1974 | Hughes ........................ 585/440 |
| 4,788,371 A | | 11/1988 | Imai et al. |
| 5,073,356 A | | 12/1991 | Guro et al. |
| 5,262,547 A | | 11/1993 | Ramachandran et al. |
| 5,276,237 A | * | 1/1994 | Mieville ........................ 585/500 |

(Continued)

FOREIGN PATENT DOCUMENTS

| | | |
|---|---|---|
| DE | 42 36 263 A1 | 4/1994 |
| EP | 0 482 276 A1 | 4/1992 |

(Continued)

OTHER PUBLICATIONS

Tonkovich et al. Experimental Investigations of Inorganic Membrane Reactors: A Distributed Feed Approach for Partial Oxidation Reactions. Chem. Eng. Sci. vol. 51, No. 5, pp. 789-806. 1996.*

(Continued)

*Primary Examiner* — Jennifer A Leung
(74) *Attorney, Agent, or Firm* — Alix, Yale & Ristas, LLP

(57) ABSTRACT

Processes for using a combination of carbon dioxide and oxygen in the dehydrogenation of hydrocarbons are provided. A hydrocarbon feedstock, carbon dioxide and oxygen are fed to an oxidative dehydrogenation reactor system containing one or more catalysts that promote dehydrogenation of the hydrocarbon feedstock to produce a dehydrogenated hydrocarbon product. The processes of the present invention may be used, for example, to produce styrene monomer by dehydrogenation of ethylbenzene using carbon dioxide and oxygen as oxidants.

17 Claims, 10 Drawing Sheets

(56) References Cited

U.S. PATENT DOCUMENTS

| | | | |
|---|---|---|---|
| 5,324,702 | A | 6/1994 | Yoo et al. |
| 6,033,632 | A | 3/2000 | Schwartz et al. |
| 6,034,032 | A | 3/2000 | Park et al. |
| 6,037,511 | A | 3/2000 | Park et al. |
| 6,117,808 | A | 9/2000 | Maiya et al. |
| 6,235,678 | B1 | 5/2001 | Mamedov et al. |
| 6,242,660 | B1 | 6/2001 | Buonomo et al. |
| 6,518,476 | B1 | 2/2003 | Culp et al. |
| 6,555,721 | B2 | 4/2003 | Griffiths et al. |
| 6,730,808 | B2 | 5/2004 | Bitterlich et al. |
| 6,958,427 | B2 | 10/2005 | Park et al. |
| 7,094,942 | B2 | 8/2006 | Abdulwahed et al. |
| 2002/0165418 | A1 | 11/2002 | Obayashi et al. |
| 2003/0155254 | A1 | 8/2003 | Mazanec et al. |
| 2003/0166984 | A1 | 9/2003 | Park et al. |
| 2004/0010174 | A1* | 1/2004 | Wang et al. ............. 585/658 |
| 2004/0034266 | A1* | 2/2004 | Brophy et al. ........... 585/658 |
| 2008/0177117 | A1 | 7/2008 | Benderly et al. |
| 2008/0302013 | A1 | 12/2008 | Repasky et al. |
| 2009/0312589 | A1 | 12/2009 | Schwint et al. |

FOREIGN PATENT DOCUMENTS

| | | |
|---|---|---|
| EP | 1 295 637 A1 | 3/2003 |
| JP | 2002-154991 | 5/2002 |
| JP | 2002-265396 A | 9/2002 |
| JP | 2004-323263 | 11/2004 |
| JP | 2005-177716 A | 7/2005 |
| JP | 2008-266286 | 11/2008 |
| WO | WO 00/14035 | 3/2000 |
| WO | WO 03/013716 A1 | 2/2003 |

OTHER PUBLICATIONS

Supplementary European Search Report dated Sep. 21, 2012 for EP Application No. 09 76 7529.

P. Belomestnykh, et al., "New preparation methods of multicomponent vanadium oxide systems . . .", Stud. Surf. Sci. Catal. (1992), 72 (New Dev. Sel. Oxid. Heterog. Catal.) 453-60.

F. Cavani, F. Trifiro, "Alternative processes for the production of styrene", Applied Catalysis A: General 133, (1995), 219-239.

J. Wang, "Ethylbenzene dehydrogenation in ZSM-5 zeolite membrane reactor", Huagong Xuebao (Chinese Edition) 57(8), (2006), 1923-1926.

U. Balachandran, et al., "Mixed-conducting membranes for hydrogen production..", Materials Research Society Symposium Proceedings (2007), 972 (Solid-State Iconics—2006), 3-13.

Y. Liu, X. Tan, K. Li, Mixed Conducting Ceramics for Catalytic Membrane Processing, Catalysis Reviews 48 (2006), 145-198.

S. Zhou, S. Wang, "Progress in selective oxidation of CO from hydrogen-rich gas", Huagong Jinzhan (2005), 24(4), 362-366.

R.L. Burwell, Jr., "Carbon monoxide removal from hydrogen-rich fuel cell feedstreams by selective catalytic oxidation", Chemtracts: Inorganic Chemistry (1993), 5(4), 209-13.

M.C. Chon, "Transformation of the old process: ethylbenzene to styrene with CO2 dilution", presentation at CHEMRAWN XVI Conference, (2003) Ottawa, Canada.

Naoki Mimura, Masahiro Saito, "Dehydrogenation of ethylbenzene to styrene over Fe2O3/Al2O3 catalysts in the presence of carbon . . . ", Catalysis Today 55(2000), 173-178.

S. Sircar, w.C. Krantz, "Simultaneous production of hydrogen and carbon dioxide from steam reformer off-gas . . . ", Separation Science and Technology 23 (14-15), (1988), 2397-415.

International Search Report for Application No. PCT/US09/47233 dated Jul. 29, 2009.

* cited by examiner

COMBINED CARBON DIOXIDE AND OXYGEN PROCESS FOR ETHYLBENZENE DEHYDROGENATION TO STYRENE

RELATED APPLICATIONS

This is a continuation of U.S. application Ser. No. 12/142,738 filed Jun. 19, 2008, now U.S. Pat. No. 8,237,000.

FIELD OF THE INVENTION

The present invention is directed to processes for using a combination of carbon dioxide and oxygen in dehydrogenation processes. The processes of the present invention may be used, for example, to produce styrene monomer by dehydrogenation of ethylbenzene using carbon dioxide and oxygen as oxidants.

BACKGROUND OF THE INVENTION

Styrene is one of the most important monomers in the modern petrochemical industry. It is used as a raw material in the production of many plastics, in particular polystyrene, as well as rubbers and resins. In 2006, United States consumption of styrene was about 14.4 billion pounds.

The most common method of production of styrene monomer (SM) is by dehydrogenation of ethylbenzene (EB). One process for production of styrene monomer from EB is by direct dehydrogenation. In this process, excess superheated steam near 800° C. is combined with EB in a low-pressure adiabatic reactor containing a potassium-promoted iron oxide catalyst. The reaction temperature is typically about 600 to 650° C. and the reaction pressure is typically about 30 to 100 kPa. The steam acts as a diluent to lower the partial pressure of the hydrogen by-product produced by the dehydrogenation reaction, allowing the reaction to proceed to a greater extent. The highly superheated steam is also the carrier of heat to drive the dehydrogenation reaction, which is highly endothermic, and the steam also decreases the amount of coke formation on the reactor catalyst by steam gasification. This process consumes high amounts of energy through the use of excess steam, and the energy required to vaporize and superheat the steam. It also has the disadvantages of catalyst deactivation and limited thermodynamic conversion.

The Lummus/UOP Smart Process is another process for conversion of EB to styrene that addresses some of the problems of direct dehydrogenation by using selective oxidation of a portion of the hydrogen by-product formed in the dehydrogenation reaction. The exothermic oxidation reaction of the hydrogen with oxygen provides at least part of the heat required for subsequent EB dehydrogenation. In addition, the removal of hydrogen from the process shifts the reaction equilibrium in the dehydrogenation unit to substantially increase single-pass EB conversions while maintaining high styrene monomer selectivity. Formation of aromatic oxidants in the reactor and $CO_2$ production can adversely affect the potassium-promoted iron oxide dehydrogenation catalyst.

More recently, the use of $CO_2$ as a mild oxidant has been proposed. In a process described in U.S. Pat. No. 6,958,427, ethylbenzene is dehydrogenated to styrene monomer in the presence of carbon dioxide as a soft oxidant over a catalyst comprising vanadium and iron, with the $CO_2$ being externally supplied from the discharge of another petrochemical process. Compared with the conventional process, the presence of carbon dioxide allows operation at a lower temperature and provides enhanced conversion and significant energy savings. The reactions taking place may be either pure $CO_2$ oxydehydrogenation, a combination of direct dehydrogenation and $CO_2$ oxydehydrogenation, where the direct dehydrogenation is followed by water-gas shift reaction within the reactor, or exclusively direct dehydrogenation followed by water-gas shift reaction within the reactor. Compared with $O_2$—ODH, the use of $CO_2$ as an oxidant avoids the explosion risks of oxygen and provides higher selectivity. The $CO_2$ also functions as a heating medium and may replace some or all of the steam used in conventional dehydrogenation processes.

The drawbacks associated with the process described in part in U.S. Pat. No. 6,958,427, the entire contents of which are incorporated herein by reference, include high investment and operating cost due to the following: 1) it still consumes a high amount of energy due to the large reaction endotherm, combined with a high carbon dioxide rate, even though it utilizes less heat requirement than the conventional direct dehydrogenation in the presence of excess steam; 2) it apparently is dependent on the continued need for superheated steam; 3) it has many heatup and cooldown steps The need for a continuous supply of $CO_2$ also limits the possible locations of the SM plant, since it must be located nearby a dedicated supply of $CO_2$. It is important to recognize that there is no net elimination of $CO_2$ by this process, despite claims that this is a "green" process. $CO_2$ is simply an oxygen carrier, which is converted to CO in the oxydehydrogenation reactor. The CO must be converted hack to $CO_2$ by the water/gas shift reactor, or used to form some other oxygenated compounds.

Park et al. from KRICT, Korea, describes a CO2 oxydehydrogenation process involving the general application of either (1) steam addition to the offgas and using a water-gas shift reaction followed by cooldown and separation of $H_2$ and $H_2O$, then recycle of the $CO_2$, or (2) separation and recycle of the $CO_2$ from the offgas, while the remaining $H_2$ and CO is further processed in a catalytic reactor to form oxygenates.

The Oxirane POSM process produces SM as a co-product beginning with the oxidation of ethylbenzene to form ethylbenzene hydroperoxide intermediate, and subsequent epoxidation of propylene with the ethylbenzene hydroperoxide to yield equi-molar amounts of propylene oxide and styrene monomer. This process is extremely capital intensive and its economics are driven by the propylene oxide market.

In addition to the processes described above, the oxidative dehydrogenation of EB using oxygen as the oxidant, the Snamprogetti/Dow SNOW™ process (concurrent dehydrogenation of ethane and ethylbenzene), the Exelus ExSyM™ process (based on toluene and methanol feedstocks), a liquid-phase ethylbenzene dehydrogenation process (Pincer catalyst technology), and processes using membranes have been considered. These processes have not been demonstrated commercially.

It would be desirable to have a process for production of styrene by dehydrogenation of EB that avoids one or more of the drawbacks of prior dehydrogenation processes.

SUMMARY OF THE INVENTION

The present invention relates to the processes for dehydrogenation of hydrocarbons using a combination of carbon dioxide and oxygen as the oxidant. The processes of the present invention are particularly suitable for the production of styrene using oxidative dehydrogenation with carbon dioxide and oxygen as oxidants. In addition to the production of styrene, a combination of $CO_2$ and $O_2$ may be used in the oxydehydrogenation processes of the present invention for the production of olefins from paraffins (e.g. ethane to ethylene, propane to propylene, n-butane to n-butene, isobutene to isobutene, etc.), and the production of di-olefins or alkynes, from paraffins and/or olefins, etc. (e.g. butadienes from n-butane or n-butenes). The combination of $CO_2$ and $O_2$ may also be used in selective oxidations, e.g. for the production of acrylonitriles, acrylic acid, acetic acid, maleic anhydride, 1,4-butanediol, ethylene oxide and propylene oxide.

The oxydehydrogenation reactor may be an oxygen-specific membrane-assisted dehydrogenation reactor. The carbon dioxide feed to the reactor may be supplied by recycled carbon dioxide from the offgas of the dehydrogenation system.

In one embodiment of the present invention, a vaporized hydrocarbon feedstock is catalytically dehydrogenated in the presence of carbon dioxide and oxygen in one or more fixed bed radial-flow reactor systems. The reactor systems may be connected in series with reheating by heat exchange or in a furnace. Part of the reaction heat requirement is provided by hot regenerated recycle gas. Part of the heat required for the process may also be provided directly inside the oxydehydrogenator(s) by exothermic reactions with $O_2$ or indirectly by injecting gas heated by exothermic oxidation reactions. The overall dehydrogenation reaction may be tuned by adjusting the amounts of carbon dioxide and oxygen to vary the overall reaction system between mildly endothermic and mildly exothermic.

Some additional alternative methods of providing heat to the reactor system include approaches that are especially suited to the use of a fluidized bed reactor system. These include multiple injection positions for the feed oxygen. This can also be done with a portion of any of the other feed streams. In addition, one approach is to utilize an external exothermic reaction with $O_2$ and feed its products into the fluidized bed reactor. Also, fluidized catalyst particles or other particles can be removed from the $CO_2/O_2$—ODH main reactor bed and heated in a separate fluidized bed vessel, e.g., by burning some hydrocarbon with air. These particles can subsequently be returned to the main reactor bed, as in an FCC system. This heating of the particles in a separate bed could also include regeneration of the catalyst. Finally, the fluidized particles could be particles that acquire oxygen in the "regenerator" and transfer that oxygen to the main reactor bed to provide the oxygen for the $CO_2/O_2$—ODH reactions.

Another special approach for providing heat input is to use an $O_2$—ODH reactor with limited oxygen feed to partially dehydrogenate the hydrocarbon feedstock and in the process heat the reaction mixture toward the conditions for the $CO_2/O_2$—ODH reactor. This approach can be used for the initial feed to the $CO_2/O_2$—ODH reactor system, and also for adding heat and reaction mixture at subsequent stages (mid-reactor, second stage, etc.) of the $CO_2/O_2$—ODH reactor system.

The output from the dehydrogenation reactors is sent to a primary separation section, where the dehydrogenation product stream is separated from unreacted hydrocarbon feedstock, condensable by-products, and offgases. The unreacted hydrocarbon feedstock is typically recycled to one or more of the dehydrogenation reactor(s). The offgas stream comprises $H_2O$, CO, $CO_2$, $H_2$ and light impurities, as well as $N_2$ if air is used as the source of oxygen. The offgas stream may be further processed to recover and recycle $CO_2$.

In one embodiment, the offgas is processed to recover $CO_2$ by compressing the offgas and subjecting it to simple oxidation for conversion of CO to $CO_2$ in an oxidizer/burner unit using oxygen or air as the oxidizing agent. The product of the oxidizer/burner unit comprises mainly carbon dioxide and some water and may be fed to a cooldown/separation unit to remove some or all of the water before recycle of the carbon dioxide. Alternatively, the product of the oxidizer/burner unit may forego the water removal and be recycled hot without cooldown.

In another embodiment of the invention, the offgas, after compression, is fed to one or more separators to remove water and hydrogen. The hydrogen gas may be recovered as a valuable co-product. The remaining gas after the separator(s) comprises mainly a $CO/CO_2$ mixture and is combined with oxygen and fed into an oxidizer/burner for conversion of CO to $CO_2$ prior to recycling the carbon dioxide.

In another embodiment of the invention, the offgas, after compression, may be combined with additional water and fed into a water-gas shift unit to convert CO in the compressed offgas into $CO_2$ and also to produce additional hydrogen. The water-gas shift unit product is fed into a cooldown/separation section to remove some or all of the water and hydrogen gas before recycle of carbon dioxide to the dehydrogenation reactors.

In yet other embodiments of the invention, an absorber system (e.g. amine or carbonate based) and/or an adsorber system (e.g. activated carbon, molecular sieves or an anchored/immobilized amine on a porous solid support) is used to first remove the $CO_2$ from the offgas. An alternative to the absorber/adsorber system is a refrigeration/cryogenic system. The reason for incorporating the absorber/adsorber is to remove $CO_2$ prior to compression. Preferably, $CO_2$ is recovered from the absorber/adsorber system at a high enough pressure for recycle. Remaining offgas volume from the absorber/adsorber system may be compressed and is comprised essentially of CO and $H_2$. The CO and $H_2$ may have further value as syngas. Alternatively, the $H_2$ may be separated as a co-product, and the CO may be fed to an oxidizer/burner unit to add additional $CO_2$ for recycle. A water-gas shift unit may be included, with $H_2O$ addition, to convert the CO to additional $H_2$ co-product and $CO_2$ for recycle.

Among the advantages of the processes of the present invention is that the combination of both carbon dioxide and oxygen for the oxydehydrogenation of ethylbenzene to styrene combines the advantages of carbon dioxide (oxydehydrogenation selectivity to styrene and heat capacity) and oxygen (e.g. exothermic heat to balance the endothermic $CO_2$—ODH reaction(s), increase in conversion by removing the dehydrogenation products CO and $H_2$). An advantage of using carbon dioxide in oxydehydrogenation reactions is that it allows operation at a lower temperature than the direct dehydrogenation due to more favorable equilibrium. One advantage of using oxygen in oxidation or oxydehydrogenation reactions is that it is energetically very favorable because the reaction is exothermic. Thus, a combination of carbon dioxide oxydehydrogenation with an oxygen-based exothermic reaction such as $O_2$—ODH or oxidation of CO and/or $H_2$ (We refer to this combination as $CO_2/O_2$ ODH) maintains the high selectivity afforded by the carbon dioxide, and the heat and conversion as afforded by the oxygen, but with lower oxygen concentrations and risks than pure oxygen oxydehydrogenation. The $CO_2/O_2$ ODH processes may operate at lower temperatures than the traditional dehydrogenation processes and even the $CO_2$—ODH processes. Other advantages of the process of the present invention will be apparent to those skilled in the art based upon the detailed description of embodiments of the invention set forth below.

DETAILED DESCRIPTION OF EMBODIMENTS OF THE INVENTION

Figure 1:
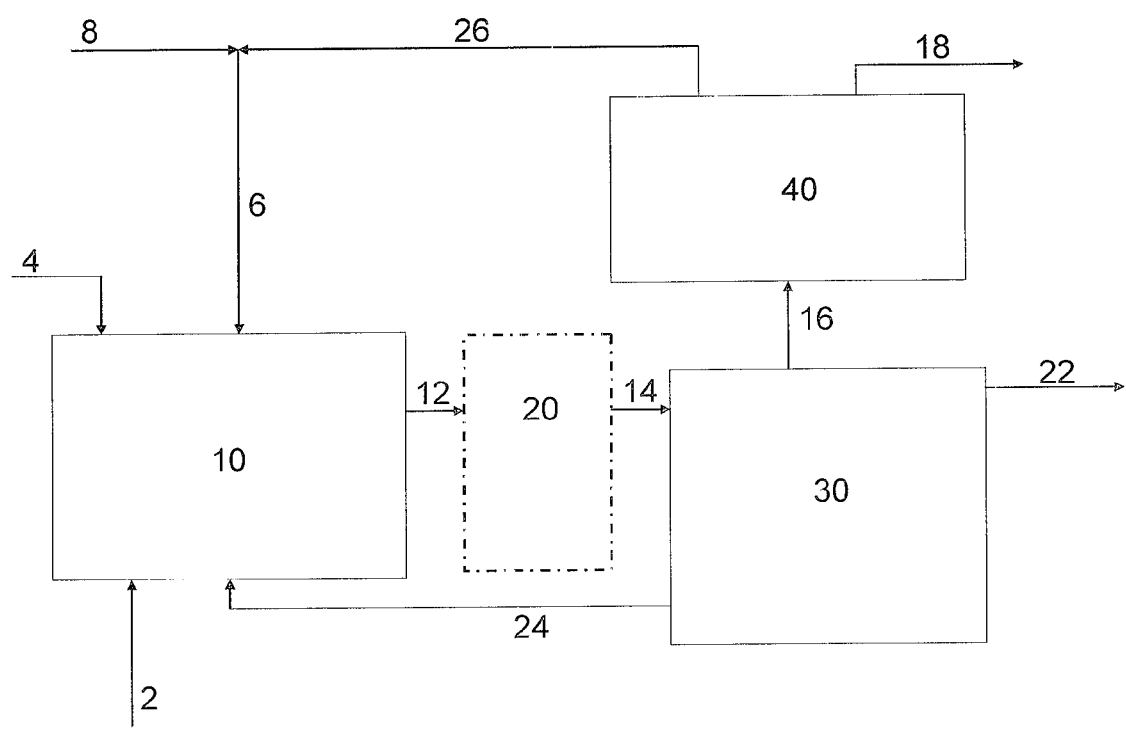
FIG. 1 is a schematic of a dehydrogenation system for performing embodiments of the process of the present invention for the oxidative dehydrogenation of feedstocks in the presence of both carbon dioxide and oxygen.

The present invention is directed to an improved process for oxidative dehydrogenation of hydrocarbon feedstocks in the presence of carbon dioxide and assisted by oxygen ($CO_2$/ $O_2$ ODH). The processes of the present invention may also incorporate by-product/offgas recovery and recycling in which recycled carbon dioxide is obtained and reused in the oxydehydrogenator system. Finally, the processes of the present invention may also incorporate the use of an oxygen-specific membrane-assisted dehydrogenation reactor in addition to various other reactor systems.

In one embodiment, the invention relates to a new dehydrogenation process for the production of styrene using $CO_2$ oxidative dehydrogenation assisted by $O_2$. The combination of both carbon dioxide and oxygen for the oxydehydrogenation of ethylbenzene to styrene combines the advantages of carbon dioxide (oxydehydrogenation selectivity to styrene and heat capacity) and oxygen (e.g. exothermic heat, increased conversion).

In particular, one advantage of using carbon dioxide in oxydehydrogenation reactions is that it allows operation at a lower temperature than the direct dehydrogenation. A disadvantage of both direct dehydrogenation and $CO_2$—ODH is that they are highly endothermic reactions and require large heat input. A major advantage of using oxygen in oxydehydrogenation reactions is that it is energetically very favorable because the reaction is exothermic. However, the use of oxygen may be disfavored because of lower selectivities to styrene with current catalyst systems, and because pure oxygen has inherent explosion risks which limit its operating regime. Oxygen may also be used to selectively oxidize CO to $CO_2$ and/or $H_2$ to $H_2O$. Here too, selectivity can be an issue, with the possibility of the $O_2$ undesirably combusting valuable feed and product compounds. A combination of carbon dioxide oxydehydrogenation with an oxygen based exothermic reaction ($CO_2$/$O_2$ ODH), selective oxidation of CO and/or $H_2$ can maintain the high selectivity afforded by the carbon dioxide, with heat and conversion enhancement provided by the oxygen reactions, but with lower oxygen concentrations and risks than pure oxygen oxydehydrogenation. The $CO_2$/$O_2$ ODH processes may, therefore, operate at lower temperatures than the traditional dehydrogenation processes (typically around 600° C.) and potentially even lower than $CO_2$—ODH processes (around 550° C.).

In one embodiment of the present invention, a vaporized feedstock is catalytically dehydrogenated in the presence of carbon dioxide in one or more fixed-bed radial-flow reactors while oxygen is fed into the reactor system. There may be more than one reactor system, which may be connected in series with reheating by heat exchanger or in a furnace. Part of the reaction heat may be provided by hot regenerated recycle gas. Part of the heat required for the process is provided directly inside the oxydehydrogenator(s) by exothermic reaction with oxygen, or indirectly by injecting gas heated by exothermic oxidation reactions. The overall dehydrogenation reaction may be tuned by adjusting the amounts of carbon dioxide and oxygen to vary the overall reaction system between mildly endothermic; and mildly exothermic.

Oxydehydrogenation offgas of the present invention comprises carbon monoxide, carbon dioxide, hydrogen, water and other reaction by-products. In one embodiment, the offgas is processed using one of several different configurations. The processing of the offgas includes producing carbon dioxide which may be recycled to the oxydehydrogenation reactor systems. For example, offgas processing may include, but is not limited to, subjecting the offgas to one or more oxidizers, separation systems, water-gas shift reactors, compressors, and/or absorbers/adsorbers.

The following detailed description of embodiments of the invention is intended to provide exemplary embodiments and is not intended to limit the full scope of the invention in any way.

Referring to FIG. 1, in one embodiment of the invention, ethylbenzene is converted to styrene in dehydrogenation reactor system(s) and the offgas, styrene, residual ethylbenzene and by-products are separated and processed. Ethylbenzene feedstock (2) may be supplied either as a fresh feed and/or a recycle feed from another process(es) and/or recycled (24) from a separation system (30) as described below. The ethylbenzene feedstock (2) and (24) is fed into a dehydrogenation reactor system (10). Oxygen (4) is fed into the dehydrogenation reactor system (10). The effluent from the dehydrogenation reactor system (10) is designated as (12). The oxygen feed (4) may be supplied as substantially pure oxygen gas and/or air, or oxygen-enriched air, or any other suitable gas containing $O_2$. Carbon dioxide (6) is also fed into the dehydrogenation reactor system (10). The carbon dioxide feed (6) is typically a combination of recycled carbon dioxide (26) and a make-up stream (8). The make-up stream (8) may be supplied either as a fresh feed and/or as a discharge gas or liquid from other process(es). In particular, $CO_2$ may be obtained as the purge stream from other petrochemical processes (e.g. ethylene oxide), from a $CO_2$ removal/recovery or transfer system, or from combustion of hydrocarbons.

The dehydrogenation reactor system (10) includes one or more catalysts to promote the oxydehydrogenation reaction in the presence of $CO_2$ and the exothermic $O_2$ "assistance" reaction(s). Catalysts known to perform $CO_2$—ODH are, for example, mixed $Fe^{II}Fe^{III}$-oxide catalysts or zirconia-based catalysts. Oxygen-based ODH catalysts can be mixed metal oxide catalysts such as Ni—V—Si/$Al_2O_3$, Ba—Ni/$Al_2O_3$, or activated carbon based catalysts. Water-gas shift catalysts (HTS) are preferably Fe—Cr-oxide catalysts. Additionally, catalysts known in the art to selectively oxidize CO to $CO_2$ and/or $H_2$ to $H_2O$ may be used. These catalysts may be noble metal based, such as, but not limited to, supported Au, Pt, Pd, Ru or Rh. Non noble metals may also be used, such as, but not limited to, supported vanadia or metal combinations such as Co—Cu, Ni—Co—Fe, Ag or Cr—Fe supported on mixed oxides.

Preferably, the catalyst system used is a $CO_2$—ODH catalyst known in the art combined with one or more of the abovementioned other catalysts. The different catalysts and their reactions may be in separate, e.g. sequential, reactors or in the same reactor. In preferred embodiments, the oxydehydrogenation reactor is operated at a temperature of between 400° C. and 700° C. and at a pressure between 10 kPa and 500 kPa.

Additional dehydrogenation reactor systems (20) may be incorporated in series with the first dehydrogenation reactor system (10). Although the present embodiment depicts one additional reactor system, it is contemplated that any number of additional reactor systems can be utilized in accordance with the present invention. Additional reactor systems may be added for various reasons, including, but not limited to, temperature control, staged feeding of the ethylbenzene, oxygen or carbon dioxide, or to provide different reactor modes. Examples of different reactor modes include type of reactor (e.g. fixed bed reactor, fluidized bed reactor, or membrane reactor). They may include or exclude additional $O_2$ feed. The complete reactor system, (10) plus (20), may include different types of dehydrogenation systems ($CO_2/O_2$—ODH, $CO_2$—ODH, $O_2$—ODH, even non-ODH if the $CO_2/O_2$—ODH systems are utilized on the effluent of a non-ODH system), and possibly water-gas shift reactor(s). Styrene product, byproducts and unreacted EB, $H_2O$ and gases from the final reactor in the system (10) or (20) are fed (14) to a primary condensation and separation section (30).

The primary condensation and separation section (30) may be essentially the same as or similar to a section typically used in conventional dehydrogenation systems. The product stream (14) is cooled to condense and separate the unreacted ethylbenzene and the styrene product and the condensible by-products from each other and from the offgas, using a combination of separation, recovery and purification systems. Styrene monomer product is removed through line (22) and sent for storage or further processing. Unreacted ethylbenzene is recycled (24) back to one or more of the oxydehydrogenation reactor systems (10) or (20). The offgas is fed (16) to an offgas section (40). In the offgas section (40) the offgas, comprising CO, $H_2O$, $CO_2$, $H_2$, and light impurities (plus $N_2$ if air is used as the $O_2$ source) is separated into $CO_2$ recycle (26) and one or more purge or co-product streams (18). There may also be some secondary recovery systems (not shown) in offgas section (40) to return products, etc. to the primary condensation and separation section (30).

The ethylbenzene feedstock (2) and recycle ethylbenzene (24) are fed to the dehydrogenation reactors at customary pressures and temperatures well known in the art. The oxygen (4) is also fed at a customary pressure and temperature as is the carbon dioxide (6) If the $CO_2$ rate is low enough that it is acceptable for its effluent amount to be totally purged, the $CO_2$ recycle (26) might be eliminated.

Preferably, the total molar feed ratios relative to total ethylbenzene (fresh feed plus recycle) are, for carbon dioxide, 0.1 to 10, and for oxygen, 0.01 to 1.0.

The present invention is applicable to the dehydrogenation of hydrocarbon feedstocks. The feedstocks may contain a single compound or contain a mixture of compounds. They may also be obtained as light cut(s) from industrial processes. Preferably, the feedstocks comprise small molecular weight hydrocarbons with average molecular weight less than 150 Daltons. In particular, the process of the present invention may be used in the production of olefins from paraffins (e.g. ethane to ethylene, propane to propylene, n-butane to n-butene, i-butane to i-butene, etc.), and the production of di-olefins or alkynes from paraffins and/or olefins, etc (e.g. butadienes from n-butane or n-butenes). The combination of $CO_2$ and $O_2$ may also be used in selective oxidations, e.g. for the production of acrylonitriles, acrylic acid, acetic acid, maleic anhydride, 1,4-butanediol, ethylene oxide and propylene oxide.

The first dehydrogenation reactor system (10) and the optional additional dehydrogenation reactor systems (20), i.e. the reactor section, may consist of one or more fixed beds, one or more fluidized beds, membrane reactor(s), or a combination of these. Ethylbenzene, $CO_2$ and $O_2$ may be fed all together, or separately, all of which may be fed to the reactor inlet(s) at once or, in addition, at several stages downstream of the inlet(s). $O_2$ is fed into at least one stage but might not be fed in all stages. The dehydrogenation catalyst(s) used in the dehydrogenation reactor system(s) are selected to promote the desired dehydrogenation reaction in the presence of carbon dioxide. Typically, at least one catalyst that promotes oxydehydrogenation by carbon dioxide is combined with at least one catalyst that promotes selective oxidation of CO and $H_2$ (or alternatively/additionally $O_2$—ODH) in the presence of oxygen.

In the reaction section for the dehydrogenation of EB to styrene according to this invention, the following main reactions may take place:

EB=Styrene+$H_2$ (direct dehydrogenation, endothermic)

EB+$CO_2$=Styrene+CO+$H_2O$ ($CO_2$—ODH, endothermic)

EB+½$O_2$→Styrene+$H_2O$ ($O_2$—ODH, exothermic)

$CO_2$+$H_2$=CO+$H_2O$ (water-gas shift, only small heat of reaction), $H_2$+½$O_2$→$H_2O$ (exothermic)

CO+½$O_2$→$CO_2$ (exothermic)

Some portion of the $O_2$ may also combust hydrocarbons. (exothermic, undesired)

Other possible reactor configurations which may be included in the present invention include utilizing the combined $CO_2/O_2$—ODH reactor section downstream of a dehydrogenation section that uses either:

Direct dehydrogenation (with neither $O_2$ nor $CO_2$)

$CO_2$—ODH (without $O_2$) or $O_2$—ODH (without $CO_2$ playing an active role other than diluent)

In another aspect of the present invention, carbon dioxide may be recovered and recycled by several recovery options. Offgas processing may include absorption, adsorption, membrane separation, further cooling/chilling/refrigeration, condensation, conversion of CO to $CO_2$ by oxidation or water-gas shift, etc. These process steps produce various possible purge streams and also affect the quantity and composition of the $CO_2$ recycle. For instance, where oxidation by $O_2$ or air is utilized to convert CO to $CO_2$ for recycle, the heat is advantageous for use as a final heating step to the reactor. The purge streams typically comprise compounds derived from $H_2$, CO, $CO_2$, $H_2O$, light impurities, and $N_2$ if present.

In one embodiment, the invention relates to new ways to handle and separate offgases of the carbon dioxide/oxygen ODH process for converting ethylbenzene to styrene wherein the offgases comprise $CO_2$, CO, $H_2$, $H_2O$, light impurities and $N_2$ if present.

Figure 2:
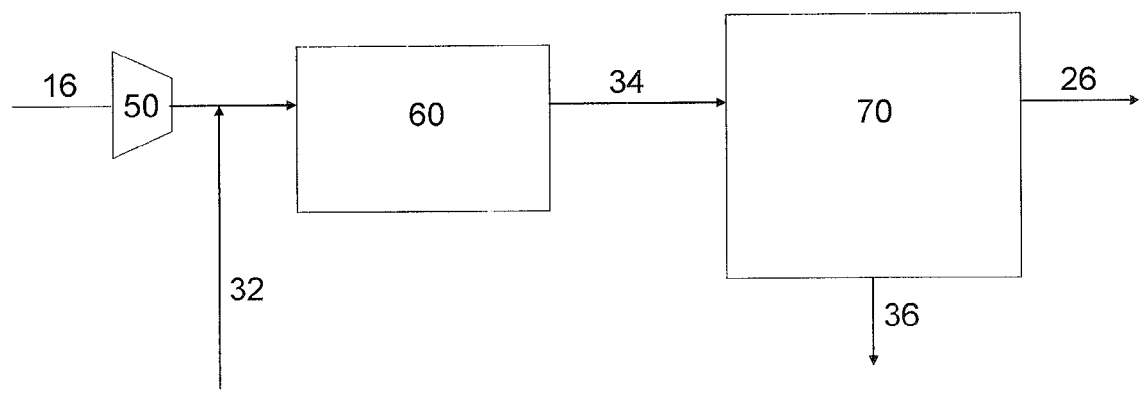
FIG. 2 is a schematic of an offgas system for performing embodiments of the process of the present invention for recovery and recycle of offgases and, in particular, the recovery and recycle of COx as carbon dioxide, oxidizing CO (and also $H_2$).

Referring to FIG. 1, the offgas (16) from the primary separation section (30) may be recycled and/or disposed of by several options. Referring to FIG. 2, in one embodiment of the invention, the complete offgas is subjected to simple oxidation using oxygen or air as the oxidizing agent after compression. The offgas feed (16) is compressed prior to being fed into an oxidizer/burner (60). Oxygen or air (32) may be fed separately to the oxidizer/burner unit (60) or mixed with the offgas feed (16) prior to the oxidizer/burner unit (60). In this and all subsequent cases, one or more purge gas stream (not shown) may be withdrawn from some position in the offgas section.

The product (34) of the oxidizer/burner unit (60) comprises mainly carbon dioxide and some water, (also $N_2$ if air is the $O_2$ source) plus a residual amount of unconverted CO and/or possibly some $O_2$ and is optionally fed (34) into a cooldown/separation unit (70) to cool the oxidizer/burner unit effluent and remove some or all of the water (36) before recycle (26) of the carbon dioxide. Alternatively, the water already present in stream (16) may be reduced or removed prior to, or both prior to and after, the burner unit (60) by arrangement of the cooldown/separation unit (70) before the oxidizer/burner unit (60) or by the addition of a second cooldown/separation unit prior to the oxidizer/burner unit (60).

Figure 3:
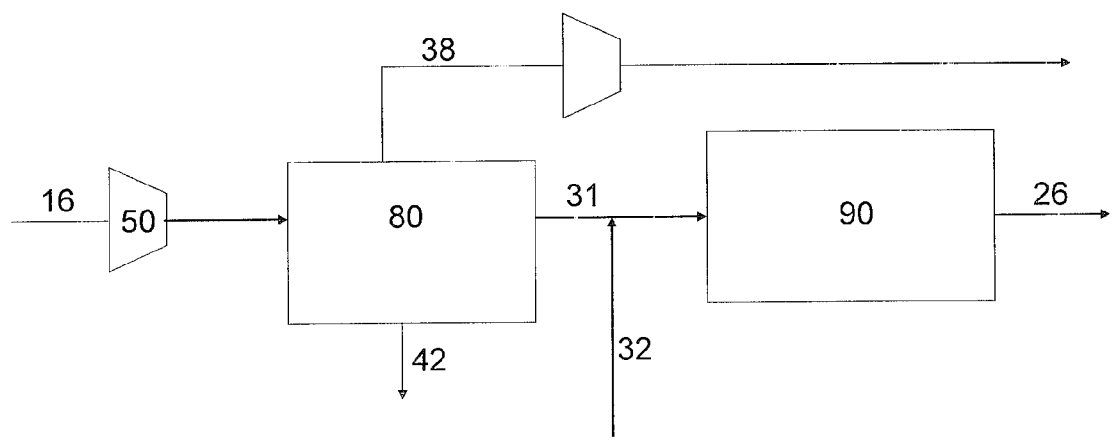
FIG. 3 is a schematic of an offgas system for performing embodiments of the process of the present invention for recovery and recycle of offgases and, in particular, the recovery and recycle of COx as carbon dioxide, separating water and $H_2$, then oxidizing CO.

Referring to FIG. 3, in one embodiment of the invention, the offgas (16), after compression (50), is fed into separators (80) to remove water (42) and hydrogen (38). The hydrogen gas (38) may be recovered downstream as a valuable co-product. The product from the separators (31) comprises mainly a $CO/CO_2$ mixture and is combined with oxygen or air (32) and fed into an oxidizer/burner unit (90) for combustion, as previously described, prior to recycling (26). The carbon dioxide recycle (26) is largely free of water (stream 26 may contain a residual amount of CO and/or $O_2$).

Figure 4:
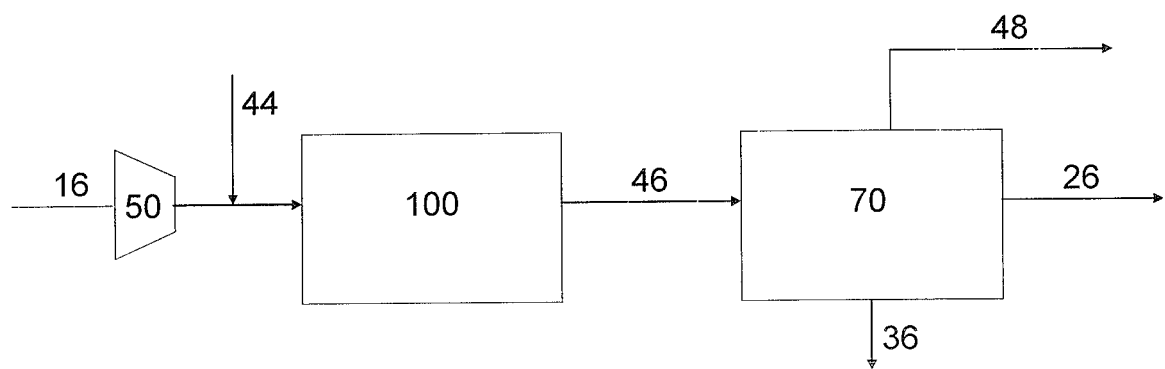
FIG. 4 is a schematic of an offgas system for performing embodiments of the process of the present invention for recovery and recycle of offgases and, in particular, the recovery and recycle of COx as carbon dioxide using a water-gas shift unit, then separating water and $H_2$.

Referring to FIG. 4, in one embodiment of the invention, the offgas (16), after compression (50), may be combined with additional water (44) and fed into a water-gas shift unit (100) to convert CO in the compressed offgas into additional $CO_2$ and also increase the hydrogen gas production. The water-gas shift unit product is fed (46) into cooldown/separation systems (70) to remove some or all of the water (36) and hydrogen gas (48) before recycle (26) of carbon dioxide.

Figure 5:
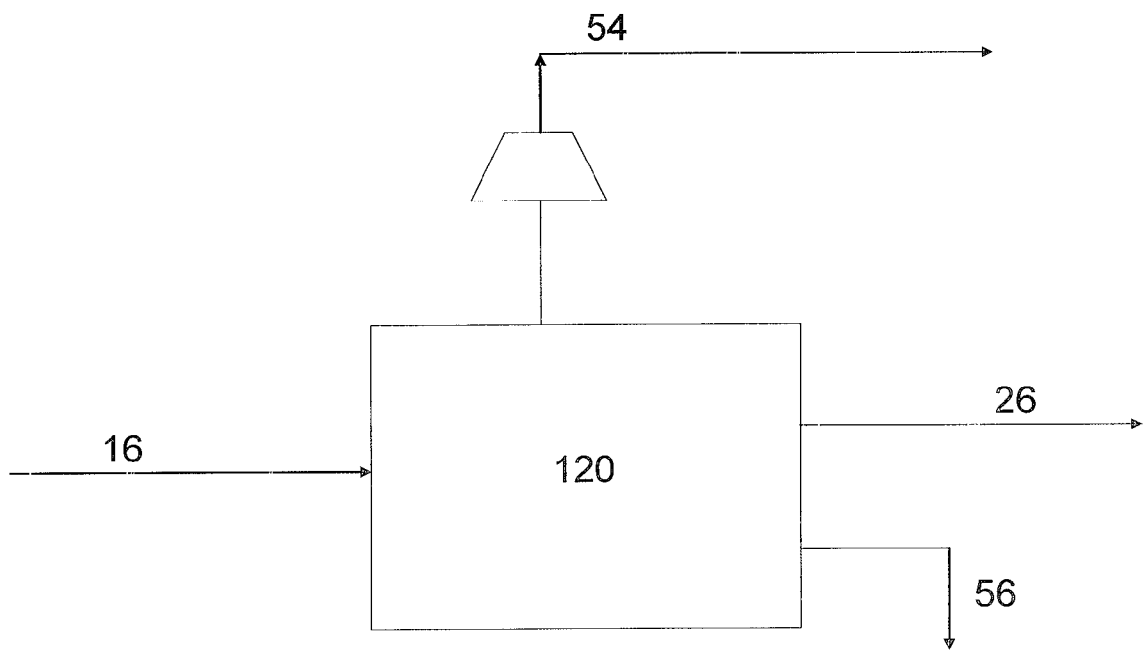
FIG. 5 is a schematic of an offgas system for performing embodiments of the process of the present invention for recovery and recycle of offgases and, in particular, the recovery and recycle of carbon dioxide using an absorber/absorber and providing an offgas containing $H_2$ and CO.

Referring to FIG. 5-9, in these embodiments of the invention, an absorber system (e.g. amine or carbonate based) and/or an adsorber system (e.g. activated carbon, molecular sieves or an anchored/immobilized amine on a porous solid support) is used to first remove the $H_2O$ and $CO_2$ from the offgas. A refrigeration/cryogenic system may be used as an alternative. The reason for incorporating the absorber/adsorber is to remove $CO_2$ prior to compression. Preferably, $CO_2$ is recovered from the absorber/adsorber system at a high enough pressure for recycle, while waste impurities and water are also removed. Remaining offgas volume from the absorber/adsorber system is greatly reduced, comprises essentially CO and $H_2$, and may be compressed for further disposition. Referring to FIG. 5 specifically, in one embodiment of the invention, the offgas (16) is fed into an absorber/adsorber system (120). Carbon dioxide (26) for recycle and water/impurities (56) are recovered from the system (120). The carbon monoxide/hydrogen mixture (54) from the system (120) is exported as co-product or for further conversion to carbon dioxide.

Figure 6:
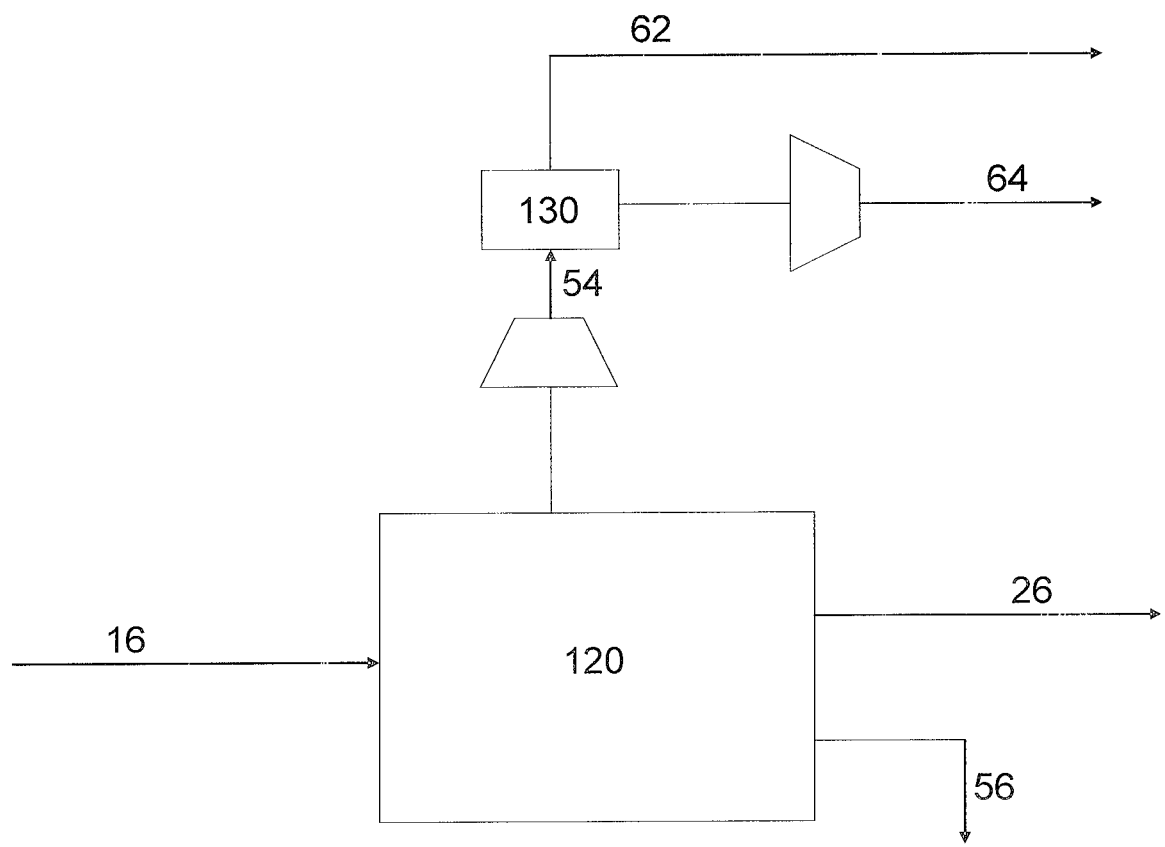
FIG. 6 is a schematic of an offgas system for performing embodiments of the process of the present invention for recovery and recycle of offgases and, in particular, the recovery and recycle of carbon dioxide using an absorber/adsorber and providing separate offgases for $H_2$ and CO.

Referring to FIG. 6, in one embodiment of the invention, the offgas (16) is fed into an absorber/adsorber system (120). Carbon dioxide (26) for recycle and water/impurities (56) are recovered from the system (120). The carbon monoxide/hydrogen mixture (54) from the system (120) is fed into a separator (130) to separate the two gases into a carbon monoxide stream (62) and a hydrogen gas stream (64). Preferably, the separator comprises a membrane separation or an activated carbon or molecular sieve adsorption system. The CO and $H_2$ gas streams (62) and (64) may be co-products and/or stream (62) may be further converted to carbon dioxide for additional recycle. If both are co-products, portions of the CO and $H_2$ streams may be recombined into a syngas stream, or less separation may be carried out to provide a syngas stream with a preferred $H_2$/CO ratio.

Figure 7:
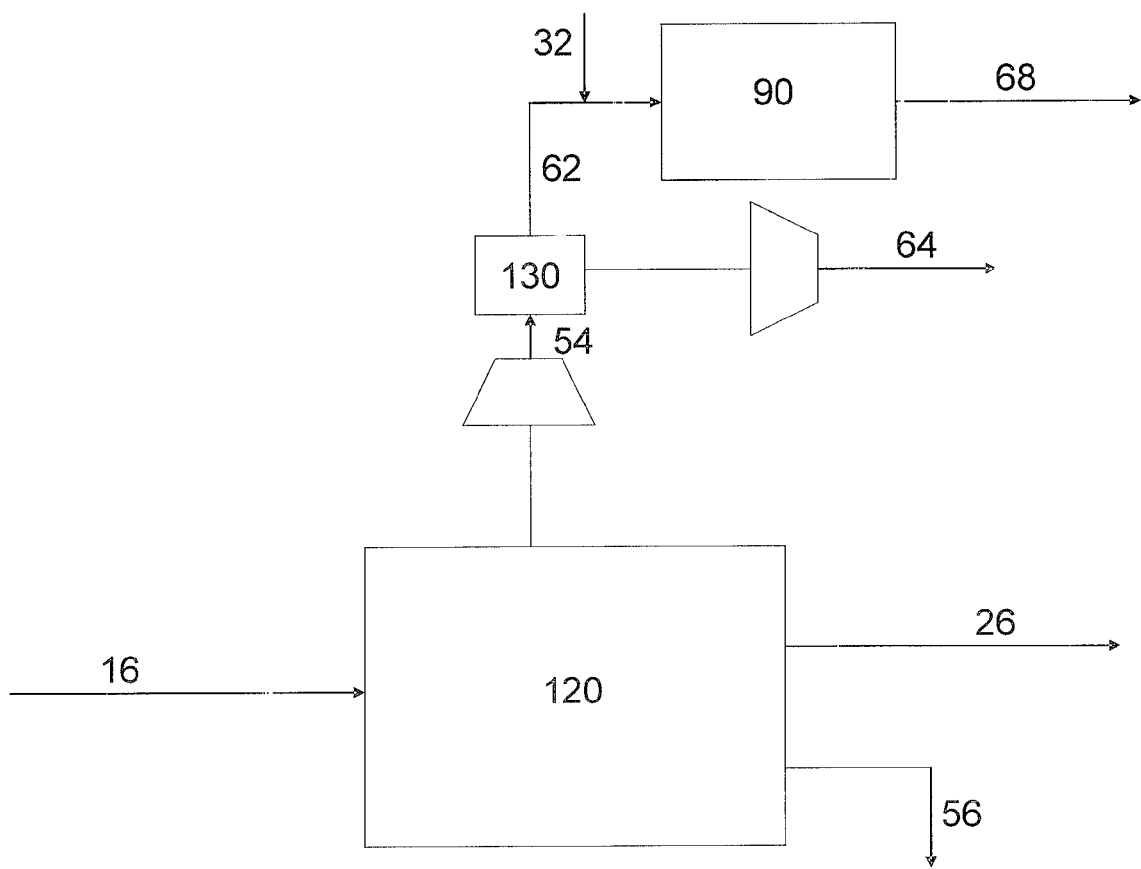
FIG. 7 is a schematic of an offgas system for performing embodiments of the process of the present invention for recovery and recycle of offgases and, in particular, the recovery and recycle of carbon dioxide using an absorber/adsorber, an offgas containing $H_2$, and oxidizing CO to $CO_2$ for additional recycle.

Referring to FIG. 7, in one embodiment of the invention, the carbon monoxide stream from FIG. 6 (62) is fed into an oxidizer/burner unit (90), and oxidized with oxygen or air (32) as previously described. The product (68) of the oxidizer/burner unit (90) comprises mainly carbon dioxide (and nitrogen if air is the source), plus a residual amount of unconverted CO and/or possibly some oxygen. This additional carbon dioxide stream (68) may be combined with the main recycle stream of carbon dioxide (26).

Figure 8:
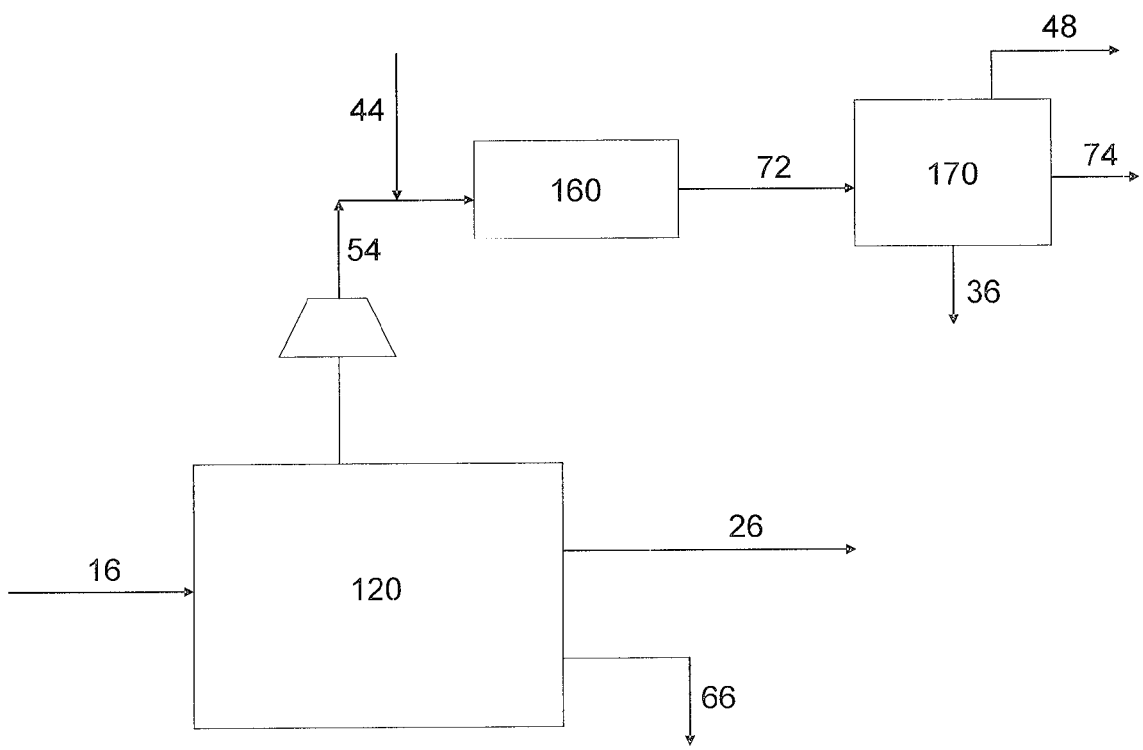
FIG. 8 is a schematic of an offgas system for performing embodiments of the process of the present invention for recovery and recycle of offgases and, in particular, the recovery and recycle of carbon dioxide using an absorber/adsorber, a water-gas shift unit to convert CO to additional $CO_2$ for recycle and $H_2O$ to additional $H_2$ co-product, followed by separation and delivery of the $CO_2$, $H_2$ and $H_2O$.

Referring to FIG. 8, in one embodiment of the invention, the carbon monoxide and hydrogen gas stream from FIG. 5 (54) may be combined with additional water (44) and fed into a water-gas shift unit (160) to convert. CO in the compressed offgas into additional $CO_2$ and also increase the hydrogen gas production. The water-gas shift product is fed (72) into cooldown/separation systems (170) to remove some or all of the water (36) and hydrogen gas (48) before recycle (74) of carbon dioxide. The additional carbon dioxide stream (74) may be combined with the main recycle stream of carbon dioxide (26).

Figure 9:
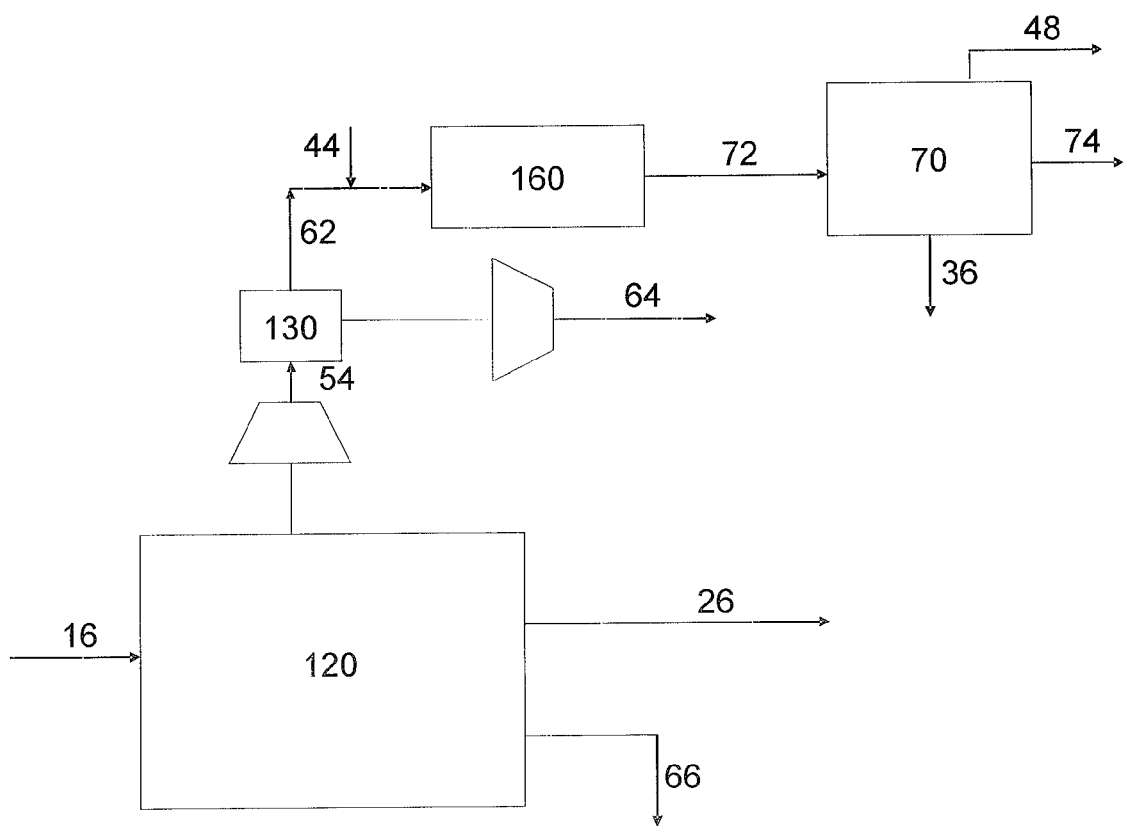
FIG. 9 is a schematic of an offgas system for performing embodiments of the process of the present invention for recovery and recycle of offgases and, in particular, the recovery and recycle of carbon dioxide using the systems of FIG. 8 plus a separator of $H_2$ prior to the water-gas shift unit in order to enhance the shift conversion to $H_2$ and $CO_2$.

Finally, referring to FIG. 9, in another embodiment of the invention, the carbon monoxide stream from FIG. 6 (62) may be combined with additional water (44) and fed into a water-gas shift unit (160) to convert CO in the compressed offgas into $CO_2$ and also increase the hydrogen gas production. The water-gas shift product is fed (72) into cooldown/separation systems (70) to remove some or all of the water (36) and hydrogen gas (48) before recycle (74) of carbon dioxide. The additional carbon dioxide stream (74) may be combined with the main recycle stream of carbon dioxide (26).

For the embodiments shown in FIGS. 2, 3 and 7, where oxidation by oxygen or air is used to convert CO to carbon dioxide for recycle, the heat produced may be utilized as a significant heating step to the reactor system.

In another embodiment of the present invention, the oxidative dehydrogenation reactor system may comprise a fluidized bed reactor system. This may facilitate the use of various additional advantageous approaches for the production of dehydrogenated hydrocarbons. These include multiple injection positions for the feed oxygen. This can also be done with a portion of any of the other feed streams. In addition, one approach is to utilize an external exothermic reaction with $O_2$ and feed its products into the fluidized bed reactor. For example, CO from the offgas section can be oxidized with oxygen and fed to the reactor to supply heat (and $CO_2$) in any number of positions within the oxidative dehydrogenation reactor system. Another example is to pass the offgas, or a portion of the offgas, from a first reactor (which can be either a fluidized bed or other reactor) to a selective oxidation reactor (which can be either a fluidized bed or other reactor) to oxidize its CO and $H_2$ and generate heat, then introduce that hot stream in any number of positions in a fluidized bed second stage $CO_2/O_2$—ODH reactor.

Another approach that is possible with a fluidized bed reactor system is to remove fluidized catalyst particles or other particles from the $CO_2/O_2$—ODH main reactor bed and heat them in a separate fluidized bed vessel, e.g. by burning some hydrocarbon with air. These particles can subsequently be returned to the main reactor bed, as in an FCC system. The particles that are moved can include the catalyst, either together with or separately from other particles, in order to regenerate the catalyst. Another possible approach with a fluidized bed system is to transfer particles between the main reactor bed and another vessel for the purpose of having the particles acquire oxygen in the other vessel. As the oxygen-charged particles are transferred back to the main reactor, they provide the oxygen for the $CO_2/O_2$—ODH reactions.

In another embodiment of the present invention, the main $CO_2/O_2$—ODH reactor system may receive part or all of its feed after this feed has been processed in an $O_2$—ODH reactor system using limited oxygen feed to partially dehydrogenate the hydrocarbon feedstock and in the process heat the reaction mixture toward the conditions for the $CO_2/O_2$—ODH reactor. This approach can be used for the initial feed to the $CO_2/O_2$—ODH reactor system, and also for adding heat and reaction mixture at subsequent stages (mid-reactor, second stage, etc.) of the $CO_2/O_2$—ODH reactor system.

In yet another embodiment of the present invention, the main $CO_2/O_2$—ODH reactor system may receive part or all of its feed after the feed has been processed in a conventional direct dehydrogenation reactor system, or a $CO_2$—ODH reactor system which does not include oxygen among its feeds. The main $CO_2/O_2$—ODH reactor system, with possible additional feed in addition to $O_2$ (e.g., $CO_2$) obtains further conversion beyond that achieved in the upstream dehydrogenation system.

In yet another embodiment of the present invention, the oxidative dehydrogenation reactor system may comprise a membrane reactor. For example, the invention may use both oxygen and carbon dioxide for the ODH of EB in a membrane reactor configuration. This configuration may be used to transport oxygen through the oxygen permeating membrane and, with the use of a suitable selective CO and hydrogen oxidation catalyst react selectively with the CO resulting from the $CO_2$—ODH reaction and hydrogen from any direct dehydrogenation reaction. This reaction provides heat for the endothermic dehydrogenation and shifts the dehydrogenation reactions to higher conversion by consuming the CO and hydrogen. In addition, the use of an oxygen-selective membrane minimizes the risk associated with the use of oxygen in a combustible gas mixture. The selectivity of the reaction may be enhanced by locating the CO and hydrogen oxidation catalyst at the membrane surface on the hydrocarbon side in order to consume the oxygen before it reaches the bulk reaction mixture Conversely, if gaseous $O_2$ mixes fully with the hydrocarbons, it may react with them indiscriminately to combust them or form oxygenates and other undesired by-products. Such a system maybe used with either air or $O_2$ gas, but may be particularly advantageous to allow the utilization of low-cost air without introducing its $N_2$ content into the reaction mixture.

Figure 10:
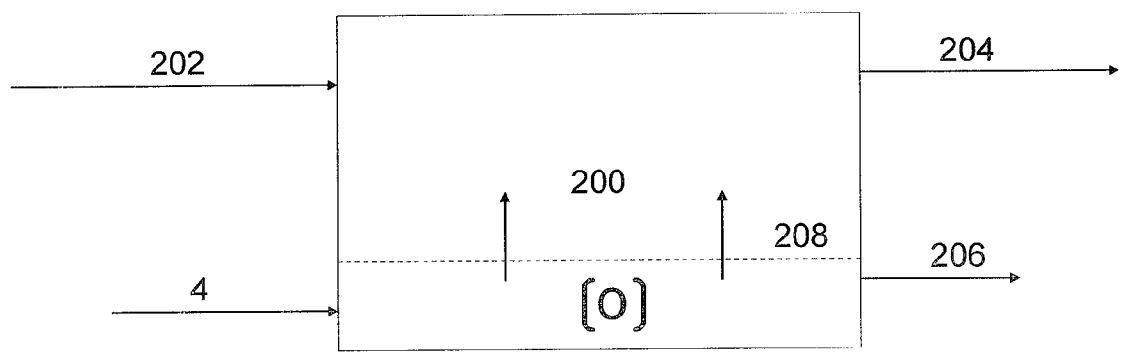
FIG. 10 is a schematic of a dehydrogenation system for performing embodiments of the process of the present invention for the oxidative dehydrogenation of feedstocks in the presence of both carbon dioxide and oxygen using an oxygen-specific membrane dehydrogenation reactor.

Referring to FIG. 10, in one embodiment of the present invention, a membrane reactor for $CO_2$—$O_2$—ODH for EB dehydrogenation to styrene is shown. Ethylbenzene and carbon dioxide are fed, together or separately, (202) into the reactor (200). The reactor comprises an oxygen permeable membrane (208). Oxygen (4) is fed into the reactor (202) at many positions. The oxygen may be supplied by pure $O_2$ gas and/or air or any other suitable gas containing $O_2$. The oxygen feed (4) enters the reactor on the side of the membrane opposite the hydrocarbon feed. The nitrogen in the air, which does not pass through the membrane, and excess oxygen are removed through line (206). The dehydrogenation product stream is removed through line (204) and sent for further processing to separate the styrene monomer from excess ethylbenzene, reaction by-products and the offgases.

In one embodiment of the present invention, the catalyst for the selective oxidation of the CO and hydrogen to $CO_2$ and water is located on the hydrocarbon feed side of the membrane. The catalyst may be either deposited on the membrane, anchored to it, and/or embedded within the membrane. In another embodiment, the membrane material itself may be an active CO and hydrogen oxidation catalyst wherein the membrane and catalyst functions are fully integrated.

Any oxygen permeable membrane material that functions under the reaction conditions may be used. Preferably, the material comprises mixed oxides such as fluorite or perovskite related structures. For example, Sr—Fe—Co oxides, La—Sr—Co—Fe oxides, Ba—Co—Fe—Zr oxides and/or Bi—Y—Sm oxides may be used. Also, any catalyst known in the industry to selectively oxidize CO and $H_2$ may be used. Preferably, the catalyst is a noble metal based catalyst, such as, but not limited to, supported Au, Pt, Pd, Ru or Rh. Non-noble metals may also be used, such as, but not limited to, supported vanadia, or metal combinations such as Co—Cu, Ni—Co—Fe, Ag or Cr—Fe supported on mixed oxides, The use of a membrane reactor provides advantages over the prior art including the anchoring of the selective oxidation catalyst on the hydrocarbon feed side of the membrane. Such anchoring may limit undesirable unselective oxidations and the injection of the oxygen may essentially be continuous from inlet to outlet instead of being limited to a few positions.

Membrane-mediated CO and $H_2$ oxidation may also provide heat for the endothermic dehydrogenation and shift the $CO_2$—ODH dehydrogenation (and any accompanying direct dehydrogenation) to higher conversion by consuming the CO and $H_2$. Moreover, a mixture of catalysts may be applied. Catalysts known in the industry to selectively oxidize CO to $CO_2$ and/or $H_2$ to $H_2O$ may be used. These catalysts may be noble metal based, such as, but not limited to, supported Au, Pt, Pd, Ru or Rh. Non-noble metals may also be used, such as, but not limited to, supported vanadia, or metal combinations such as Co—Cu, Ni—Co—Fe, Ag or Cr—Fe supported on mixed oxides. The CO and $H_2$ oxidation catalyst(s) in this membrane configuration may be combined with an oxygen ODH catalyst for the conversion of ethylbenzene to styrene. Alternatively, a multi-functional catalyst may be used that combines the selective CO oxidation with any one or more of the abovementioned reactions, or even with the primary $CO_2$—ODH reaction.

The scope of the present invention is not limited to the examples provided based on the conversion of ethylbenzene to styrene. In addition to application for the production of styrene using $CO_2/O_2$—ODH, the present invention contemplates the use of a selective CO and $H_2$ oxidation membrane reactor configuration in $CO_2/O_2$—ODH for the production of olefins (e.g. ethane to ethylene, propane to propylene, n-butane to n-butenes, isobutane to isobutene, etc.), and the production of di-olefins or alkynes from paraffins and/or olefins, etc (e.g. butadiene from n-butane or n-butenes). In addition to application for ODH, the use of a selective CO and $H_2$ oxidation membrane reactor configuration may potentially be used in selective partial oxidations where $CO_2$ is used as a soft oxidant (e.g. for the production of acrylonitrile, acrylic acid, acetic acid, maleic anhydride, 1,4-butanediol, ethylene oxide and propylene oxide.)

While preferred embodiments have been shown and described, various modifications may be made to the processes described above without departing from the spirit and scope of the invention as described in the appended claims. Accordingly, it is to be understood that the present invention has been described by way of example and not by limitation.

What is claimed is:

1. A system for dehydrogenation of a hydrocarbon stream comprising:
   (a) a dehydrogenation reactor containing an oxygen-selective membrane that separates the reactor into first and second gas passages, the oxygen-selective membrane being configured to transport oxygen from the second gas passage to the first gas passage;
   (b) a first reactor inlet configured to feed hydrocarbon feedstock and carbon dioxide into the first gas passage;
   (c) a second reactor inlet configured to feed oxygen into the second gas passage for subsequent transport through the oxygen-selective membrane;
   (d) a carbon dioxide oxidative dehydrogenation catalyst disposed in the first gas passage to react carbon dioxide, oxygen and hydrocarbon to produce a dehydrogenation product stream, and
   (e) a separation section including a first separator configured to separate the dehydrogenation product stream into a dehydrogenated hydrocarbon product stream, an unreacted hydrocarbon stream, and an offgas stream comprising carbon monoxide and carbon dioxide, and a second separator-configured to separate carbon monoxide in the offgas stream from carbon dioxide.

2. The system of claim 1, further including an $O_2$ oxydehydrogenation reactor upstream from the dehydrogenation reactor.

3. The system of claim 1, wherein the separation section includes a condenser.

4. The system of claim 3, further including an absorber/adsorber downstream from the condenser, the absorber/adsorber being configured to remove carbon dioxide from the offgas stream prior to compression.

5. The system of claim 4, further comprising a third carbon dioxide recycle line configured to introduce carbon dioxide removed from the absorber/adsorber into the first reactor inlet.

6. The system of claim 1, wherein the separation section includes a compressor configured to compress the offgas stream.

7. The system of claim 6, wherein the separation section includes an oxidizer disposed downstream from the compressor, the oxidizer being configured to convert compressed carbon monoxide into carbon dioxide.

8. The system of claim 7, further including a first carbon dioxide recycle line configured to introduce carbon dioxide removed from the oxidizer into the first reactor inlet.

9. The system of claim 7, wherein the second separator is disposed between the compressor and the oxidizer.

10. The system of claim 6, further comprising a water-gas shift unit downstream from the compressor, the water-gas shift unit being configured to convert carbon monoxide in the offgas stream to carbon dioxide, producing a water-gas shift unit effluent.

11. The system of claim 10, further including a second carbon dioxide recycle line configured to introduce carbon dioxide removed from the water-gas shift unit into the first reactor inlet.

12. The system of claim 1, wherein the catalyst is disposed on the oxygen-selective membrane.

13. The system of claim 1, wherein the membrane itself comprises a selective carbon monoxide and hydrogen oxidation catalyst.

14. The system of claim 1, wherein the catalyst is a multi-function catalyst for carbon monoxide oxidation and hydrocarbon dehydrogenation.

15. The system of claim 1, wherein the second reactor inlet includes at least two oxygen feed points into the second gas passage.

16. A system for dehydrogenation of a hydrocarbon stream comprising:
   (a) a dehydrogenation reactor containing an oxygen-selective membrane that separates the reactor into first and second gas passages, the oxygen-selective membrane being configured to transport oxygen from the second gas passage to the first gas passage;
   (b) a first reactor inlet configured to feed hydrocarbon feedstock and carbon dioxide into the first gas passage;
   (c) a second reactor inlet configured to feed oxygen into the second gas passage for subsequent transport through the oxygen-selective membrane;
   (d) a carbon dioxide oxidative dehydrogenation catalyst disposed in the first gas passage to react carbon dioxide, oxygen and hydrocarbon to produce a dehydrogenation product stream,
   (e) a separation section including a condenser configured to condense a portion of the dehydrogenation product stream, a first separator configured to separate a dehydrogenated product stream from an unreacted hydrocarbon stream, a compressor configured to compress an offgas stream from the condenser, and at least one of an oxidizer and a water-gas shift unit configured to convert carbon monoxide in the offgas stream to carbon dioxide, and
   (f) an absorber/adsorber disposed between the condenser and the compressor configured to remove carbon dioxide from the offgas stream prior to compression.

17. The system of claim 16, further comprising at least one recycle line configured to introduce carbon dioxide removed from the separation section into the first reactor inlet.

* * * * *